(12) United States Patent
Komatsu et al.

(10) Patent No.: US 7,132,524 B2
(45) Date of Patent: Nov. 7, 2006

(54) PLANT BRASSINOLIDE RESPONSIVE GENES AND USE THEREOF

(75) Inventors: Setsuko Komatsu, Tsukuba (JP); Guangxiao Yang, Tsukuba (JP)

(73) Assignees: National Agriculture and Bio-oriented Research Organization, Ibaraki (JP); National Institute of Agrobiological Sciences, Ibaraki (JP)

( * ) Notice: Subject to any disclaimer, the term of this patent is extended or adjusted under 35 U.S.C. 154(b) by 390 days.

(21) Appl. No.: 10/303,996

(22) Filed: Nov. 26, 2002

(65) Prior Publication Data

US 2003/0217390 A1   Nov. 20, 2003

(30) Foreign Application Priority Data

May 20, 2002   (JP)  ............................. 2002-145183

(51) Int. Cl.
  *C12N 15/29* (2006.01)
(52) U.S. Cl. ..................................... 536/23.6
(58) Field of Classification Search ............... 536/23.1, 536/23.6; 435/320.1, 419, 468; 800/278, 800/298, 290
  See application file for complete search history.

(56) References Cited

U.S. PATENT DOCUMENTS 5,925,807 A * 7/1999 Chiang et al. ............... 800/298
2004/0016025 A1 * 1/2004 Budworth et al. ........... 800/287

FOREIGN PATENT DOCUMENTS

EP        1 033 405 A2     9/2000

OTHER PUBLICATIONS

Kano-Murakami et al (1993, FEBS 334:365-368).*
Yang, G. and Komatsu, S., "cDNA cloning and characterization of a brassinolide-enhanced gene OsBLE II in rice seedlings," presented at the 24th Annual Meeting of the Molecular Biology Society of Japan, Abstract No. 2P-082, p. 494, Yokohama, Japan (Nov. 2001).
English translation of Yang, G. and Komatsu, S., "cDNA cloning and characterization of a brassinolide-enhanced gene OsBLE II in rice seedlings," presented at the 24th Annual Meeting of the Molecular Biology Society of Japan, Abstract No. 2P-082, p. 494, Yokohama, Japan (Nov. 2001).
Yang, G. and Komatsu, S., "Molecular characterization of OsBLE2, a novel brassinolide-enhanced gene in rice seedlings," *FEBS J.*, Suppl. 1, Abstract No. PS1-017, p. 39, Blackwell Publishing (Oct. 2002).
Sharma, A., et al., "Antisense inhibition of a BRI1 receptor reveals additional protein kinase signaling components downstream to the perception of brassinosteroids in rice," *FEBS Lett.* 507:346-350, Elsevier Science B.V. (Oct. 2001).
Yamamuro, C., et al., "Loss of Function of a Rice *brassinosteroid insensitive1* Homolog Prevents Internode Elongation and Bending of the Lamina Joint," *Plant Cell* 12:1591-1605, American Society of Plant Physiologists (2000).
NCBI Entrez, GenBank Report, Accession No. AB072977 (Apr. 3, 2002).
NCBI Entrez, GenBank Report, Accession No. AB072978 (Apr. 3, 2002).
NCBI Entrez, GenBank Report, Accession No. C26961, Yamamoto, K. and Sasaki, T., Entry date 1997.

* cited by examiner

*Primary Examiner*—Stuart F. Baum
(74) *Attorney, Agent, or Firm*—Sterne, Kessler, Goldstein & Fox P.L.L.C.

(57) ABSTRACT

The objective of the present invention is to isolate and identify genes responsive to plant hormones, such as, brassinolide, and to provide these genes and their use. The present inventors found two novel genes (referred to as OsBLE1 gene and OsBLE2 gene) whose expressions are markedly increased by brassinolide and auxin, using DNA microarray techniques and Northern blotting. Transformed rice plants were produced using *Agrobacterium* EHA101 which comprise antisense polynucleotide against OsBLE1 and OsBLE2 under the control of the CaMV35S promoter in a binary vector pIG121-Hm. As a result, the transformed rice plants exhibited inhibition in stem and leaf growth as compared with controls which carried the vector alone.

1 Claim, 5 Drawing Sheets

Control   OsBLE1
          antisense

Control   OsBLE2
          antisense

PLANT BRASSINOLIDE RESPONSIVE GENES AND USE THEREOF

FIELD OF THE INVENTION

The present invention relates to the plant hormone-responsive genes, OsBLE1 and OsBLE2, and their use.

BACKGROUND OF THE INVENTION

Dwarfism in plants can be achieved by artificial mutagenesis via chemicals and radiation. However, these methods cause undesirable mutations in genes other than the gene involved in plant dwarfism. Moreover, the dwarf phenotype is largely hetero-recessive and therefore it is difficult to select desired transformed plants when additional genetic traits are to be added.

The dwarfism techniques employing recent biotechnology procedures can overcome the problems described above, in which plant shapes are controlled by introducing a single specific gene or antisense DNA into plants. The dwarf phenotype is inherited by subsequent generations as a dominant trait according to Mendelian inheritance.

A known method for controlling plant shapes using biotechnology is that of controlling gibberellin biosynthesis. For example, a method of dwarfing a plant by introducing the gibberellin 2β hydroxylase gene into the plant has been reported (Sakamoto T, et al., Plant Physiol., 25: 1508–1516, 2001). A method for semi-dwarfing a plant by introducing the antisense DNA against the gibberellin 3β hydroxylase gene into the plant has also been reported (Ito H, et al., Proc. Natl. Acad. Sci. USA, 98: 8909–8916, 2001).

Brassinosteroids are a new class of plant hormones which function to enhance plant cell division, elongation and differentiation. Research of brassinosteroids has been underway, but the molecular mechanism of action thereof is not yet fully understood.

SUMMARY OF THE INVENTION

This need in the art led to the present invention, and the objective of the present invention is to isolate and identify genes responsive to plant hormones like brassinosteroid, and to provide these genes and their use. More specifically, the objective of the present invention is to provide the plant hormone-responsive genes, OsBLE1 and OsBLE2, and a method for dwarfing plants by suppressing the expression of these genes.

To understand the molecular mechanism of brassinosteroid action, the present inventors treated the base of leaf blades of rice seedling with brassinolide (a type of brassinosteroid) and searched via the DNA microarray technique for a gene cluster in which the expression of the genes was controlled by brassinolide. As a result of their research, the present inventors identified 12 different genes in which expression was dependent on brassinolide concentration. The present inventors further performed Northern blots to analyze the expression pattern of these 12 genes. As a result, the present inventors identified two different genes (referred to as the OsBLE1 gene and the OsBLE2 gene) whose expressions were markedly increased following brassinolide and auxin treatment. Full length OsBLE1 and OsBLE2 cDNAs were isolated by the 5' RACE method based on EST information and these genes were found to be novel. Furthermore, transformed rice plants were produced using *Agrobacterium* EHA101 comprising antisense DNAs against OsBLE1 and OsBLE2 under the control of the CaMV35S promoter in a binary vector, pIG121-Hm. Results showed that these transformed rice plants showed inhibition in stem and leaf growth as compared to controls (which carried the vector alone).

Specifically, the present invention provides a first polynucleotide selected from the group consisting of:

(a) a polynucleotide encoding a polypeptide comprising the amino acid sequence of SEQ ID NO: 2 or 4;

(b) a polynucleotide comprising a coding region of the nucleotide sequence of SEQ ID NO: 1 or 3;

(c) a polynucleotide encoding a polypeptide comprising the amino acid sequence of SEQ ID NO: 2 or 4, in which one or more of the amino acids are substituted, deleted, added, and/or inserted; and (d) a polynucleotide hybridizing under stringent conditions with a polynucleotide comprising the nucleotide sequence of SEQ ID NO: 1 or 3. Preferably, the above first polynucleotide is used to enhance plant growth.

The present invention also provides a second polynucleotide that is used to dwarf a plant, the second polynucleotide selected from the group consisting of:

(a) a polynucleotide encoding an antisense RNA complementary to a transcript of the above first polynucleotide;

(b) a polynucleotide encoding an RNA having ribozyme activity that specifically cleaves a transcript of the above first polynucleotide;

(c) a polynucleotide encoding an RNA that suppresses expression of the above first polynucleotide due to RNA interference (RNAi) when expressed in a plant cell;

(d) a polynucleotide encoding an RNA that suppresses expression of the above first polynucleotide due to cosuppression when expressed in a plant cell; and (e) a polynucleotide encoding a polypeptide having a dominant negative phenotype for a polypeptide encoded by the above first polynucleotide.

In addition, the present invention also provides a vector comprising the above first or second polynucleotide.

Furthermore, the present invention relates to a transformed plant cell comprising the above first or second polynucleotide in an expressible manner.

The present invention also relates to a transformed plant comprising the above transformed plant cell and to a transformed plant which is a progeny or a clone of the above transformed plant.

Furthermore, the present invention features a propagation material of the above transformed plants.

Another feature of the present invention is a method for producing the above transformed plant, the method comprising the steps of:

introducing the above first or second polynucleotide into a plant cell; and then regenerating the plant from the plant cell.

Another feature of the present invention is a method for dwarfing a plant where the above first polynucleotide is endogenous, the method comprising the step of suppressing expression of the above first polynucleotide in a cell of this plant. Preferably, in this method the above second polynucleotide is introduced into this plant.

BRIEF DESCRIPTION OF THE DRAWINGS

FIG. 2A indicates that the expression of the genes is induced two to six hours after brassinolide treatment. FIG. 2B indicates that the expression of the genes was increased in the leaf sheath and the base of the leaf blades in rice. FIG. 2C indicates that the expression of the genes increased following auxin (IAA), gibberellin ($GA_3$), or brassinolide (BL) treatment.

FIG. 4A is a control.

DETAILED DESCRIPTION OF THE INVENTION

Figure 1A:
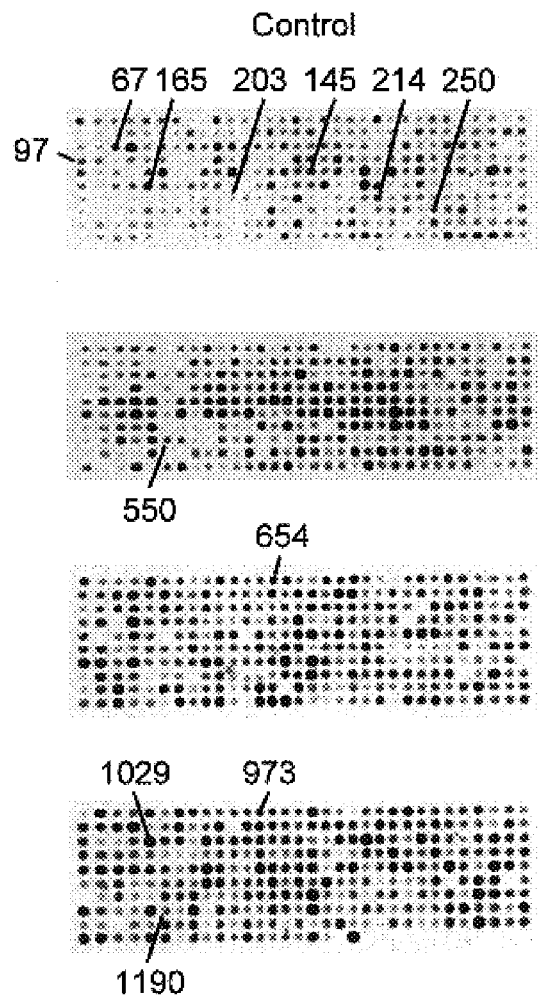
FIGS. 1A and 1B are photographs which show, using a DNA microarray technique, the increase in the expression of genes after treating the base of leaf blades of rice seedlings with brassinolide (BL). The numbers in the figures indicate the 12 different genes whose expression was markedly increased following brassinolide treatment.

The present invention provides polynucleotides encoding OsBLE1 and polynucleotides encoding OsBLE2. Preferably, the polynucleotides have properties to be expressed in response to plant hormones in plants.

The polynucleotides can be derived from any plant, including rice, wheat, barley and fruit trees.

According to the present invention, plant hormones preferably include brassinosteroids (for example, brassinolide) or auxin; however, they are not limited thereto. Brassinosteroid as used herein refers to a plant growth regulator with a steroid backbone. It is known that brassinosteroids have many functions, such as enhancement of plant growth and plant maturation, and induction of cold resistance. Brassinolide is a type of brassinosteroid. Auxin as used herein refers to a plant growth regulator with an indole backbone. It is known that some important roles of plant auxins include plant growth and differentiation, formation of flower buds and fruits, and responses to light and gravity.

Polynucleotides encoding OsBLE1 of the present invention include, for example, a polynucleotide comprising the coding region of the nucleotide sequence of SEQ ID NO: 1 and a polynucleotide encoding a polypeptide comprising the amino acid sequence of SEQ ID NO: 2. Polynucleotides encoding OsBLE2 of the present invention include, for example, a polynucleotide comprising the coding region of the nucleotide sequence of SEQ ID NO: 3 and a polynucleotide encoding a polypeptide comprising the amino acid sequence of SEQ ID NO: 4.

The phrase "isolated polynucleotide," as used herein, refers to a polynucleotide whose structure is not identical to that of any naturally occurring nucleic acid, or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., those occurring in a DNA library like cDNA or genomic DNA library.

Accordingly, one aspect of the invention provides an isolated polynucleotide that encodes a polypeptide described herein or a fragment thereof. Preferably, the isolated polypeptide includes a nucleotide sequence that is at least 60% identical to the nucleotide sequence shown in SEQ ID NO: 1 or 3. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NO: 1 or 3. In the case of an isolated polynucleotide which is longer than or equivalent in length to the reference sequence, e.g., SEQ ID NO: 1 or 3, the comparison is made with the full length of the reference sequence. Where the isolated polynucleotide is shorter than the reference sequence, e.g., shorter than SEQ ID NO: 1 or 3, the comparison is made to a segment of the reference sequence of the same length (excluding any loop required by the homology calculation).

The present invention includes a polynucleotide encoding a polypeptide that is structurally similar to OsBLE1 of SEQ ID NO: 2 or OsBLE2 of SEQ ID NO: 4 and that has function for enhancing plant growth. Preferably, such polynucleotide has property for expressing in response to plant hormones in plants.

Whether or not a polynucleotide encodes a polypeptide having function of enhancing plant growth can be determined by, for example, observing whether or not growth of plants transformed with the polynucleotide is enhanced or whether or not plants transformed with another polynucleotide which suppress the expression of the polynucleotide are dwarfed.

Furthermore, whether or not a polynucleotide encodes a polypeptide expressing in response to plant hormones can be determined by, for example, examining whether or not the polypeptide or mRNA encoding the polypeptide is induced, depending on the treatment with the plant hormones, in plants transformed with the polynucleotide.

Examples of such polynucleotides include mutants, derivatives, alleles, variants, and homologs which encode polypeptides comprising the amino acid sequence of SEQ ID NO: 2 or 4 in which one or more of the amino acids are substituted, deleted, added, and/or inserted.

An example of a method for preparing a polynucleotide encoding a polypeptide comprising altered amino acid sequence, which method is well known to those skilled in the art, includes site-directed mutagenesis (Kramer W and Fritz H-J, Methods Enzymol. 154: 350 (1987)). The amino acid sequence of a polypeptide may also be mutated in nature due to a mutation of the nucleotide sequence encoding the polypeptide. A polynucleotide encoding a polypeptide having the amino acid sequence of wild-type OsBLE1 (SEQ ID NO: 2) or OsBLE2 (SEQ ID NO: 4) in which one or more of the amino acids are substituted, deleted, added, and/or inserted may also be included in the polynucleotides encoding OsBLE1 or OsBLE2 of the present invention, so long as it encodes a polypeptide functionally equivalent to the wild-type OsBLE1 or OsBLE2. The number of amino acids that are mutated is not particularly restricted, as long as the polynucleotide of the present invention encodes a polypeptide functionally equivalent to the wild-type OsBLE1 (SEQ ID NO: 2) or OsBLE2 (SEQ ID NO: 4). Normally, it is within 50 amino acids, preferably within 30 amino acids, more preferably within 10 amino acids, and even more preferably within 3 amino acids. The site of mutation may be any site, as long as the polynucleotide of the present invention encodes a polypeptide functionally equivalent to the wild-type OsBLE1 (SEQ ID NO: 2) or OsBLE2 (SEQ ID NO: 4). Additionally, nucleotide sequence mutants that do not give rise to any amino acid sequence mutations in the polypeptide (degeneracy mutants) are also included in the polynucleotides encoding OsBLE1 or OsBLE2 of the present invention.

An amino acid substitution is preferably mutated into different amino acid(s) in which the properties of the amino acid side-chain are conserved. A "conservative amino acid substitution," as employed in the present invention, refers to a replacement of one amino acid residue belonging to one of the following groups with similar side chain(s) with another amino acid from the same group. Groups of amino acid residues having similar side chains are well known to one of ordinary skill in the art. These groups include the following: amino acids with basic side chains (e.g., lysine, arginine, histidine); acidic side chains (e.g., aspartic acid, glutamic acid); uncharged polar side chains (e.g., glycine, asparagine, glutamine, serine, threonine, tyrosine, cysteine); nonpolar side chains (e.g., alanine, valine, leucine, isoleucine, proline, phenylalanine, methionine, tryptophan); beta-branched side chains (e.g., threonine, valine, isoleucine); and aromatic side chains (e.g., tyrosine, phenylalanine, tryptophan, histidine).

Another method for preparing polynucleotide encoding a polypeptide functionally equivalent to OsBLE1 of SEQ ID NO: 2 or OsBLE2 of SEQ ID NO: 4, the method which is well known to those skilled in the art, is, for example, a method using hybridization techniques (Southern E M, J. Mol. Biol., 98: 503, 1975) and the polymerase chain reaction (PCR) technique (Saiki R K, et al., Science, 230: 1350, 1985; Saiki R K, et al., Science, 239: 487, 1988). That is, it is routine for those skilled in the art to isolate a polynucleotide with high homology to the OsBLE1 gene or OsBLE2 gene from rice and other plants using the nucleotide sequence of OsBLE1 gene (SEQ ID NO: 1) or OsBLE2 gene (SEQ ID NO: 3), or parts thereof as a probe, and oligonucleotides hybridizing specifically to the nucleotide sequence as a primer. Such polynucleotide encoding polypeptides functionally equivalent to OsBLE1 or OsBLE2, the polynucleotide that can be isolated by hybridization technique and PCR technique, is included in the polynucleotides encoding OsBLE1 or OsBLE2 of this invention.

Hybridization reactions to isolate such polynucleotides are preferably conducted under stringent conditions. The stringent hybridization conditions of the present invention refer to conditions comprising: 6 M urea., 0.4% SDS, and 0.5×SSC, and those having a stringency equivalent to the conditions. Polynucleotides with higher homology are expected to be isolated when hybridization is performed under conditions with higher stringency, for example, 6 M urea, 0.4% SDS, and 0.1×SSC. Herein, "high homology" means an identity of at least 50% or more, more preferably 70% or more, further more preferably 90% or more, and most preferably 95% or more, in the whole amino acid sequence.

The degree of identity at amino acid sequence level or nucleotide sequence level can be determined by using the BLAST algorithm by Karlin and Altschul (Karlin S and Altschul S F, Proc. Natl. Acad. Sci. USA, 87: 2264–2268, 1990; Karlin S and Altschul S F, Proc. Natl. Acad. Sci. USA, 90: 5873–5877, 1993). The BLAST algorithm-based programs, called BLASTN and BLASTX, have been developed (Altschul S F, et al., J. Mol. Biol. 215: 403, 1990). When a nucleotide sequence is analyzed according to BLASTN, parameters are set, for example, at score=100 and word length=12. On the other hand, parameters used for the analysis of amino acid sequences by BLASTX are set, for example, at score=50 and word length=3. Default parameters of each program are used when BLAST and Gapped BLAST programs are used. Specific procedures for such analysis are known.

Polynucleotides of the present invention include a genomic DNA, a cDNA, and a chemically synthesized DNA. There is no restriction on length of the polynucleotide of the present invention, but it preferably comprises at least 15 nucleotides. A genomic DNA and cDNA can be prepared according to conventional methods known to those skilled in the art. More specifically, the genomic DNA can be prepared, for example, as follows: (i) extracting genomic DNA from rice cultivars comprising the OsBLE1 gene or the OsBLE2 gene; (ii) constructing a genomic library (using, for example, a plasmid, phage, cosmid, BAC, PAC, as a vector); (iii) spreading the library; and then (iv) conducting colony hybridization or plaque hybridization using probes prepared based on the polynucleotide (e.g. SEQ ID NO: 1 or 3) encoding OsBLE1 or OsBLE2 of the present invention. Alternatively, the genomic DNA can be prepared by PCR, using primers specific to a polynucleotide (e.g., SEQ ID NO: 1 or 3) encoding OsBLE1 or OsBLE2 of the present invention. On the other hand, the cDNA can be prepared, for example, as follows: (i) synthesizing cDNAs based on mRNA extracted from rice cultivars comprising the OsBLE1 gene or the OsBLE2 gene; (ii) constructing a cDNA library by inserting the synthesized cDNA into vectors, such as λZAP; (iii) spreading the cDNA library; and (iv) conducting colony hybridization or plaque hybridization as described above. Alternatively, the cDNA can also be prepared by PCR.

Polynucleotides encoding OsBLE1 or OsBLE2 of the present invention can be used, for example, to produce a transformed plant with enhanced elongation. Such transformed plants can be produced by: (i) inserting the polynucleotides into an appropriate vector; (ii) introducing the vector into a plant cell; and (iii) regenerating the plant from the resulting transformed plant cell. OsBLE1 or OsBLE2 gene isolated by the present inventors can be introduced into any plant and then expressed, resulting in enhancement of elongation in the plant.

The present invention revealed that inhibition of the expression of OsBLE1 or OsBLE2 gene causes dwarfism in plants. The present invention also provides a method for dwarfing plants. A transformed plant with dwarf phenotype can be obtained, for example, by: inserting polynucleotides which inhibit the expression of OsBLE1 and OsBLE2 genes into an appropriate vector; introducing the vector into a plant cell; and regenerating the plant from the resulting transformed plant cell. The step of suppressing the expression of polynucleotides encoding OsBLE1 or OsBLE2 includes suppressing transcription of the gene as well as suppressing translation thereof into a polypeptide. It also includes not only complete cessation of expression of the polynucleotide but also reduction in expression thereof. It also includes the inhibition of the in vivo function of the translated polypeptide inside a plant cell.

The expression of a specific endogenous gene in plants can be suppressed via methods which are commonly used in the art, such as, methods utilizing antisense technology. Ecker et al. were the first to demonstrate the antisense effect of an antisense RNA introduced by electroporation into plant cells (Ecker J R and Davis R W, Proc. Natl. Acad. Sci. USA 83: 5372, 1986). Thereafter, target gene expression was reportedly reduced in tobacco and petunias by expressing antisense RNAs (van der Krol A R, et al. Nature 333: 866, 1988). As a result, antisense techniques are now well established as a means to suppress target gene expression in plants.

Multiple factors are required for antisense nucleic acid to suppress target gene expression. These include: inhibition of transcription initiation by triple strand formation; inhibition of transcription by hybrid formation at the site where the RNA polymerase has formed a local open loop structure; transcription inhibition by hybrid formation with the RNA being synthesized; inhibition of splicing by hybrid formation at the junction between an intron and an exon; inhibition of splicing by hybrid formation at the site of spliceosome formation; inhibition of mRNA translocation from the nucleus to the cytoplasm by hybrid formation with mRNA; inhibition of splicing by hybrid formation at the capping site or at the poly A addition site; inhibition of translation initiation by hybrid formation at the binding site for the translation initiation factors; inhibition of translation by hybrid formation at the site for ribosome binding near the initiation codon; inhibition of peptide chain elongation by hybrid formation in the translated region or at the polysome binding sites of mRNA; and inhibition of gene expression by hybrid formation at the sites of interaction between nucleic acids and polypeptides. In other words, antisense nucleic acids suppress target gene expression by inhibiting various processes, such as, transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)", Nihon Seikagakukai (The Japanese Biochemical Society) eds., Tokyo Kagaku Dozin, pp. 319–347, (1993)).

An antisense sequence of the present invention can suppress the target gene expression by any of the above mechanisms. In one embodiment, if an antisense sequence is designed to be complementary to the untranslated region near the 5' end of the gene's mRNA, it will effectively inhibit translation of a gene. It is also possible to use sequences complementary to the coding regions or to the untranslated region on the 3' side. Thus, the antisense polynucleotide used in the present invention includes polynucleotide having antisense sequences against both the untranslated regions and the translated regions of the gene. The antisense polynucleotide to be used is connected downstream from an appropriate promoter, and, preferably, a sequence containing the transcription termination signal is connected on the 3' side. The polynucleotide thus prepared can be transfected into the desired plant by using known methods. The sequence of the antisense polynucleotide is preferably a sequence complementary to the endogenous gene of the plant to be transformed or a part thereof, but it need not be perfectly complementary so long as it can effectively inhibit the gene expression. The transcribed RNA is preferably 90% or more, and most preferably 95% or more complementary to the transcription products of the target gene. In order to effectively suppress the expression of the target gene by means of an antisense sequence, the antisense polynucleotide should have at least 15 nucleotides or more, preferably 100 nucleotides or more, and most preferably 500 nucleotides or more. The antisense polynucleotide to be used is generally shorter than 5 kb, and preferably shorter than 2.5 kb.

Polynucleotide encoding ribozymes can also be used to suppress the expression of endogenous genes. A ribozyme is a RNA molecule that has catalytic activity. There are many ribozymes having various activities. Research focusing on ribozymes as RNA-cleaving enzymes has enabled the design of a ribozyme that site-specifically cleaves RNA. While some ribozymes of the group I intron type or the Ml RNA contained in RNaseP consist of 400 nucleotides or more, others belonging to the hammerhead type or the hairpin type have an activity domain of about 40 nucleotides (Makoto Koizumi and Eiko Ohtsuka, Tanpakushitsu Kakusan Kohso (Nucleic acid, Protein, and Enzyme), 35: 2191, 1990).

The self-cleavage domain of a hammerhead type ribozyme cleaves at the. 3' side of C15 of the sequence G13U14C15. Formation of a nucleotide pair between U14 and A9 is considered important for the ribozyme activity. Furthermore, it has been shown that the cleavage also occurs when A15 or U15 exists instead of C15 (Koizumi M, et al., FEBS Lett 228: 228, 1988). If the ribozyme in which the substrate binding site is complementary to the RNA sequences adjacent to the target site is designed, one can create a restriction-enzyme-like RNA cleaving ribozyme which recognizes the sequence UC, UU, or UA within the target RNA (Koizumi M, et al., FEBS Lett 239: 285, 1988; Makoto Koizumi and Eiko Ohtsuka, Tanpakushitsu Kakusan Kohso (Protein, Nucleic acid, and Enzyme), 35: 2191, 1990; Koizumi M, et al., Nucleic Acids Res. 17: 7059, 1989). For example, in the polynucleotide encoding OsBLE1 or OsBLE2 (SEQ ID NO: 1 or 3), there is a plurality of sites that can be used as the ribozyme target.

The hairpin type ribozyme is also useful for the purpose of the present invention. This ribozyme can be found, for example, in the minus strand of the satellite RNA of tobacco ringspot virus (Buzayan J M., Nature 323: 349, 1986). It has also been shown that a target-specific RNA-cleaving ribozyme can be prepared from hairpin type ribozyme (Kikuchi Y and Sasaki N, Nucleic Acids Res. 19: 6751, 1991; Yo Kikuchi, Kagaku To Seibutsu (Chemistry and Biology) 30: 112, 1992).

The ribozyme designed to cleave the target is linked with a promoter, such as the cauliflower mosaic virus 35S promoter, and with a transcription termination sequence, so that it gets transcribed in plant cells. If extra sequences have been added to the 5' end or the 3' end of the transcribed RNA, the ribozyme activity may be lost. In this case, one can place an additional trimming ribozyme, which functions in cis on the 5' or the 3' side of the ribozyme portion, in order to precisely cut the ribozyme portion from the transcribed RNA containing the ribozyme (Taira K, et al., Protein Eng. 3: 733, 1990; Dzaianott A M, and Bujarski J J, Proc. Natl. Acad. Sci. USA 86: 4823, 1989; Grosshans C A, and Cech T R, Nucl Acids Res. 19: 3875, 1991; Taira K, et al., Nucl Acids Res. 19: 5125, 1991). One can achieve greater effects by arranging these structural units in tandem to allow multiple sites within the target gene to be cleaved (Yuyama N, et al., Biochem. Biophys. Res. Commun. 186: 1271, 1992). As described above, it is possible to suppress the expression of the gene by specifically cleaving the transcripts of the target gene of the present invention using ribozymes.

Endogenous gene expression can also be suppressed by RNA interference (RNAi) using double stranded RNA which comprises a sequence identical or similar to the target gene. RNAi refers to the phenomenon in which a double stranded RNA having a sequence identical or similar to the target gene sequence is introduced into cells, and thereby expression of both the introduced exogenous gene and the target endogenous gene is suppressed. The detailed mechanism of RNAi is unknown, but it is thought that double stranded RNA which was introduced is first degraded into small pieces and serves as an index of the target gene in an unknown manner, resulting in degradation of the target genes. It is known that RNAi is effective in plants (Chuang C F, Meyerowitz E M, Proc Natl Acad Sci USA 97: 4985, 2000). For example, in order to inhibit the expression of polynucleotides encoding OsBLE1 or OsBLE2 in plants by RNAi, polynucleotides encoding OsBLE1 or OsBLE2 or double stranded RNAs having a sequence similar to the polynucleotides can be introduced into the plants in question, and a plant that is dwarfed compared with a wild-type plant can be selected from the resultant plants. The gene to be used for RNAi need not be completely identical to the target gene; however, it should have at least 70% or more sequence identity, preferably 80% or more, more preferably 90% or more, and most preferably 95% or more sequence identity. Sequence identity can be determined by methods described previously (see the paragraph describing BLAST algorithm).

Endogenous gene expression can also be suppressed by cosuppression through the transformation by polynucleotide which has a sequence identical or similar to the target gene sequence. The term "cosuppression" as used herein refers to the phenomenon in which, when a gene having a sequence identical or similar to the target endogenous gene sequence is introduced into plants by transformation, expression of both the introduced exogenous gene and the target endogenous gene becomes suppressed. Although the detailed mechanism of cosuppression is unknown, it is predicted that it is identical to the mechanism of RNAi at least partially. Cosuppression is also observed in plants (Smyth D R, Curr Biol 7: R793, 1997; Martienssen R, Curr Biol 6: 810, 1996). For example, in order to obtain a plant in which the polynucleotide encoding OsBLE1 or OsBLE2 are cosuppressed, the plant in question can be transformed with a vector polynucleotide prepared so as to express the polynucleotide encoding OsBLE1 or OsBLE2 or polynucleotide having a similar sequence, and then a plant that is dwarfed compared with a wild-type plant can be selected from the resultant plants. The gene to be used for cosuppression does not need to be completely identical to the target gene, but it should have at least 70% or more, preferably 80% or more, more preferably 90% or more, and most preferably 95% or more sequence identity. Sequence identity may be determined by methods described previously (see the paragraph describing BLAST algorithm).

In addition, endogenous gene expression of the present invention can also be suppressed by transforming plants with a gene encoding a polypeptide having a dominant negative phenotype for a polypeptide encoded by the target gene. Herein, "a gene encoding a polypeptide having a dominant negative phenotype" refers to a gene which, when expressed, functions to eliminate or reduce the activity of the wild type endogenous polypeptide produced in the plant occurring in nature.

The present invention provides a method of producing a transformed plant, the method comprising the steps of introducing the polynucleotide of the present invention into a plant cell and regenerating plants from these cells.

There is no limitation as to the plants from which cells used for the present invention are derived. Vectors used for the transformation of plant cells are not limited as long as they can express the inserted gene in the plant cells. For example, vectors comprising promoters (e.g., cauliflower mosaic virus 35S promoter) for constitutive gene expression in plant cells and vectors comprising promoters that are inducibly activated by exogenous stimuli can be used. The term "plant cell" used herein includes various forms of plant cells, such as suspension culture cells, protoplasts, leaf sections, and callus.

A vector can be introduced into plant cells by various methods known to those skilled in the art, such as polyethylene glycol method, electroporation, *Agrobacterium* mediated transformation, and particle bombardment. Particle bombardment can be carried out by, for example, using the equipment available from Bio-Rad. Plants can be regenerated from transformed plant cells by methods known to one skilled in the art, according to the type of plant cell (Toki S, et al., Plant Physiol., 100: 1503, 1992).

For example, methods for producing transformed rice plants include the following: (1) method of introducing genes into protoplasts by polyethylene glycol and regenerating the plants (suitable for Indica rice cultivars) (Datta S K: In Gene Transfer To Plants (Potrykus I and Spangenberg, Eds) pp. 66–74, 1995); (2) method of introducing genes into protoplasts via electric pulses and regenerating the plants (suitable for *Japonica* rice cultivars) (Toki S, et al., Plant Physiol., 100: 1503, 1992); (3) method of introducing genes directly into cells by particle bombardment and regenerating the plants (Christou P, et al., Biotechnology 9: 957, 1991); and (4) method of introducing genes using *Agrobacterium* and regenerating the plants (for example, the ultrahigh-speed transformation of monocotyledons (Japanese Patent No. 3141084)). The methods listed above are well established and are widely used in the technical field of the present invention. Hence, these methods can be suitably used in the present invention.

Once a transformed plant is obtained in which the polynucleotide of the present invention is introduced into the genome, it is possible to obtain progenies from the plant by sexual or asexual propagation. Alternatively, plants can be mass-produced from propagation materials (for example, seeds, fruits, grafts, tubers, tuberous roots, roots, callus, protoplast) obtained from the plant, as well as progenies or clones thereof.

The transformed plant of the present invention can be used to produce the polypeptide encoded by the polynucleotide of the present invention. The resulting polypeptide is useful for isolating an antibody that binds to the polypeptide. The isolated antibody can be utilized to purify or detect the polypeptide of the present invention. Thus, the present invention also relates to a polypeptide encoded by the polynucleotide of the present invention; and a method for producing the polypeptide, the method comprising use of the transformed plant of the present invention.

The term "substantially pure" as employed herein, in reference to a given polypeptide, means that the polypeptide is substantially free from other biological macromolecules. The substantially pure polypeptide is at least 75% (e.g., at least 80, 85, 95, or 99%) pure by dry weight. Purity can be measured by any appropriate standard method, such as, column chromatography, polyacrylamide gel electrophoresis or HPLC analysis.

It is widely known that plant hormones control growth of each plant organ. However, very little is known about brassinolide. The present invention discloses a technique for dwarfing a plant using genes which is induced by exogenous brassinolide. This technique is different from the conventional methods, which use genes involved in gibberellin biosynthesis. The present invention makes it possible to inhibit rice plants, for example, from lodging under high concentration of nitrogen. The lodging reduces yield and quality of rice.

Any patents, patent applications and publications cited herein are incorporated by reference in their entirety.

Herein, "%" for concentration denotes weight per volume percent, unless otherwise specified.

The present invention will be specifically described below using examples, but is not to be construed as being limited thereto.

(1) Plant Materials and Treatment

Rice (Nipponbare) was grown at 25° C. and 75% humidity with a 12-hrs day and 12-hrs night under white fluorescent light (about 600 $\mu mol \cdot m^{-2} sec^{-1}$). Commercially available, high quality brassinolide (BL), gibberellin (GA), and indole-3-acetic acid (IAA) were used for the present invention. The method of Chomczynski and Sacchi (Chomczynski P., Sacchi N., Ana. Biochem., 162: 156–159, 1987) was used to extract RNA for RNA blotting analysis. An mRNA purification kit oligotex-dT-30 (Takara), was used to prepare mRNA for micro-array analysis.

(2) Microarray Analysis

A cDNA microarray containing 1265 EST clones was used. RNA was isolated from the base of leaf blades treated with 1 μM brassinolide for 48 hours. Reverse transcription reaction was performed for two hours at 42° C. using 1 μg of mRNA in the presence of 50 μM Cy5 dCTP (Amersham Pharmacia), and then stopped. After heated at 94° C. for 3 min, the resulting mixture was treated with NaOH at 37° C. for 15 min to digest the RNA, and then cDNA was recovered. Fluorescently labeled cDNA probe was purified using a QIA quick PCR purification kit (Qiagen). Probe hybridization and microarray slide scanning were carried out according to the method of Yazaki et al. (Yazaki J., et al. DNA Research 7: 367–370: 2000). Data were analyzed according to Array Vision (Imaging Research).

(3) RNA Extraction and Northern Blotting Analysis

After tissue samples were quickly frozen in liquid nitrogen, about 0.5 g of the frozen tissue was ground into powder in a mortar and pestle. Total RNA was prepared by the method of Chomczynski and Sacchi (Chomczynski P., Sacchi N., Anal. Biochem., 162: 156–159, 1987). Then, mRNA for microarray analysis was purified from the total RNA using oligotexdT kit (Takara). For Northern blot analysis, 20 μg of the total RNA were electrophoresed in a 1.2% agarose gel containing 6% formaldehyde and then transferred to a Hybond™-N⁺ nylon membrane. In order to ensure equivalent amount of RNAs were electrophoresed for Northern blotting, the present inventors stained gels with ethidium bromide to compare rRNA quantity. Hybridization was carried out at 42° C. overnight using ULTRAhyb™ (Ambion), and the membrane was washed with 2×SSC and 0.1% SDS at 42° C. for 5 min, and then with 0.1×SSC and 0.1% SDS at 68° C. for 15 min. Nylon membrane was exposed to X-ray film (Kodak).

(4) Full Length cDNA Cloning

As EST clones are partial cDNAs, the present inventors screened rice leaf-derived cDNA library (Zhang Z. , Komatsu S., J. Biochem., 128: 383–389, 2000) to clone a full length cDNA Moreover, the present inventors isolated 5' end of cDNA using SMART™ PCR cDNA synthesis kit (Clontech) and determined the nucleotide sequence of the cDNA using a sequencer from Applied Biosystem.

(5) Rice Transformation

Two different cDNAs were inserted into an expression vector in the antisense direction. The resulting vector was then introduced into Agrobacterium (EHA101). The resulting Agrobacterium was used to transform Nipponbare rice cultivar by the ultrahigh-speed transformation method for monocotyledons (Japanese Patent No. 3141084).

EXAMPLE 1

Figure 1B:
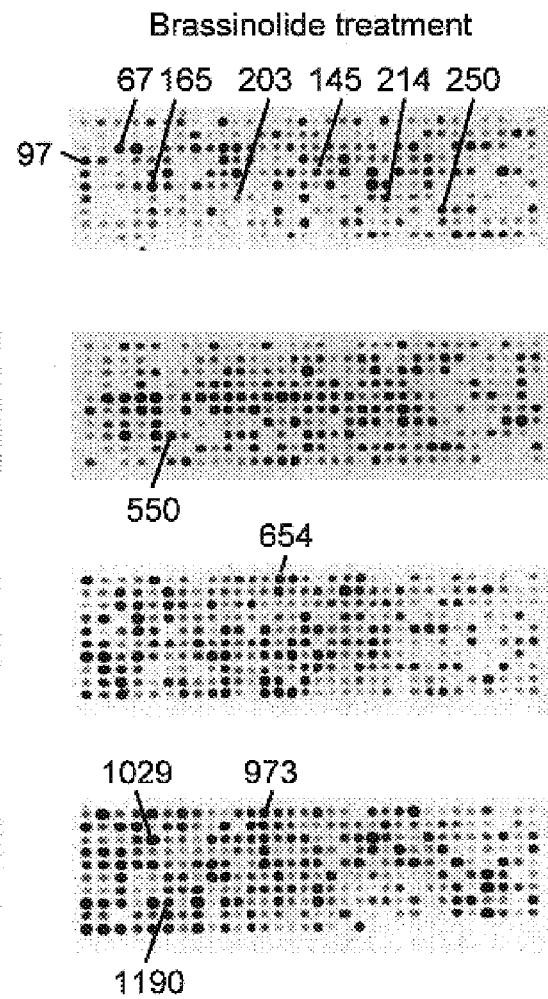

Total RNA was extracted from the base of leaf blades of rice (Nipponbare) seedling treated with 1 μM brassinolide, and the RNA was analyzed using cDNA microarrays containing 1265 rice genes. The results indicated that expression level of the 12 different genes markedly increased depending on the concentration of brassinolide (FIGS. 1A and 1B). EST (expression tag) clones for use were obtained in the Rice Genome Project of the Ministry of Agriculture, Forestry, and Fisheries of Japan and are available from the homepage thereof. Most of the EST clones had cDNAs with unknown functions. Thus, it was impossible to predict, from only their partial cDNA sequences, whether expression increase of the 12 genes depends on the presence of brassinolide.

Total RNA was extracted from the base of leaf blades of rice (Nipponbare) seedling treated with 1 μM brassinolide, and the RNA was analyzed using cDNA microarrays containing 1265 rice genes. The results indicated that expression level of the 12 different genes markedly increased depending on the concentration of brassinolide (FIGS. 1A and 1B). EST (expression tag) clones for use were obtained in the Rice Genome Project of the Ministry of Agriculture, Forestry, and Fisheries of Japan and are available from the homepage thereof (http://microarray.rice.dna.affrc.go.jp). Most of the EST clones had cDNAs with unknown functions. Thus, it was impossible to predict, from only their partial cDNA sequences, whether expression increase of the 12 genes depends on the presence of brassinolide.

EXAMPLE 2

Figure 2A:
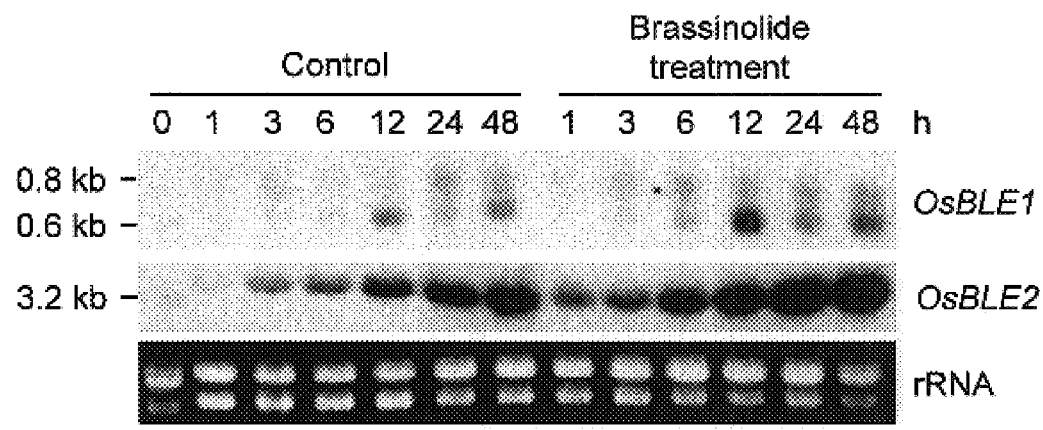
FIGS. 2A–2C are photographs which show the expression of two different genes (OsBLE1 and OsBLE2) whose expression was found to be increased after brassinolide treatment.
Figures 2B, 2C:
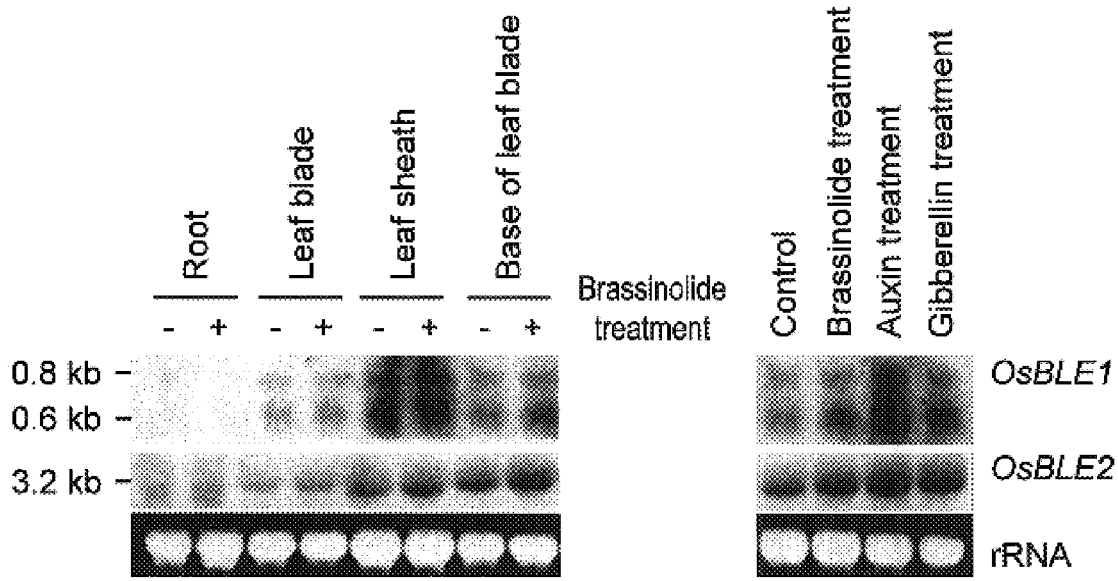
Figure 3:
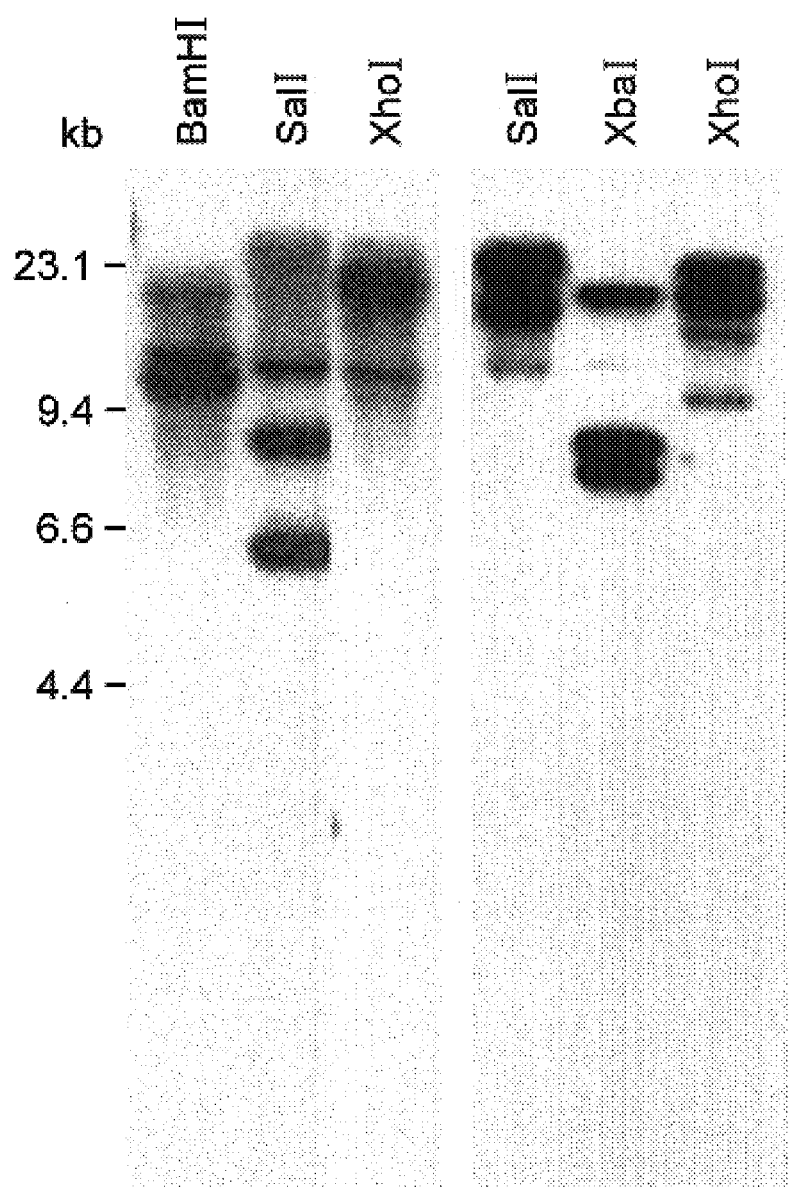
FIG. 3 is a photograph which shows the results of Southern hybridization analysis. The results indicate that rice chromosomal DNA contains at least two copies of each of OsBLE1 gene (left) and OsBLE2 gene (right).

The expression patterns of the 12 genes were analyzed by Northern blotting. The present inventors then found two genes whose expression occurs one to six hours after brassinolide treatment and was increased in the leaf sheath and the base of leaf blades by auxin and brassinolide treatment (FIGS. 2A–2C). The present inventors named these two genes OsBLE1 and OsBLE2.

EXAMPLE 3

The present inventors isolated full length OsBLE1 and OsBLE2 cDNAs using the 5' RACE method based on the EST information and found that OsBLE1 comprised 598 nucleotides (SEQ ID NO: 1) encoding 81 amino acids (SEQ ID NO: 2) and that OsBLE2 comprised 3243 nucleotides (SEQ ID NO: 3) encoding 761 amino acids (SEQ ID NO: 4). The present inventors found no significant sequence homology between amino acid sequences predicted from the genes and that in the database. Therefore, both genes found were novel.

EXAMPLE 4

Genomic DNA from Nipponbare rice cultivar was digested with restriction enzymes BamHI, SalI, XhoI, and XbaI, and then subjected to Southern hybridization using OsBLE1 and OsBLE2 cDNAs as probe. As shown in FIG.

3, multiple bands were observed. Therefore, it was predicted that there were at least two copies of each of OsBLE1 and OsBLE2 genes in the chromosomal DNA.

EXAMPLE 5

Figure 4A:
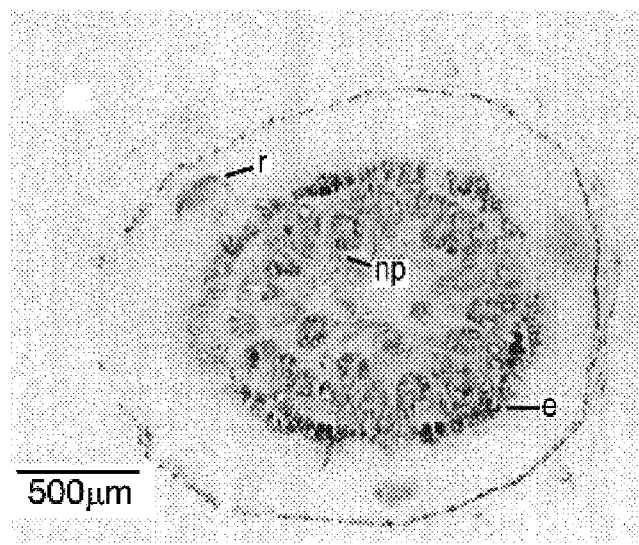
FIGS. 4A–4C are photographs depicting the distribution of OsBLE1 and OsBLE2 genes expression in in situ hybridization. The results indicate that both OsBLE1 (FIG. 4B) and OsBLE2 (FIG. 4C) genes are expressed in the base of root (r) and internodal parenchyma (np).
Figure 4B:
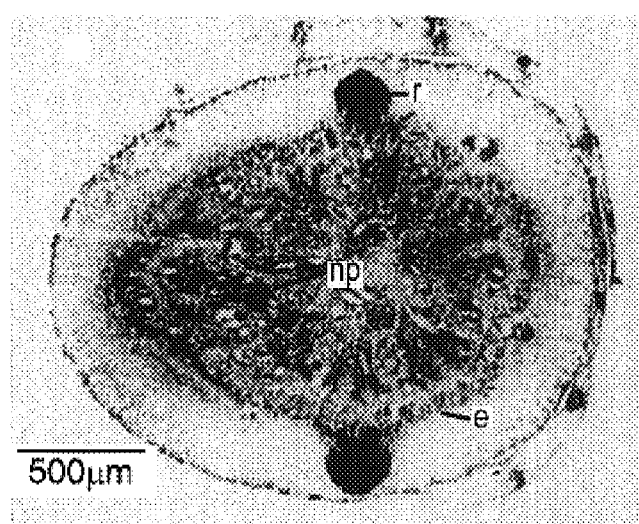
Figure 4C:
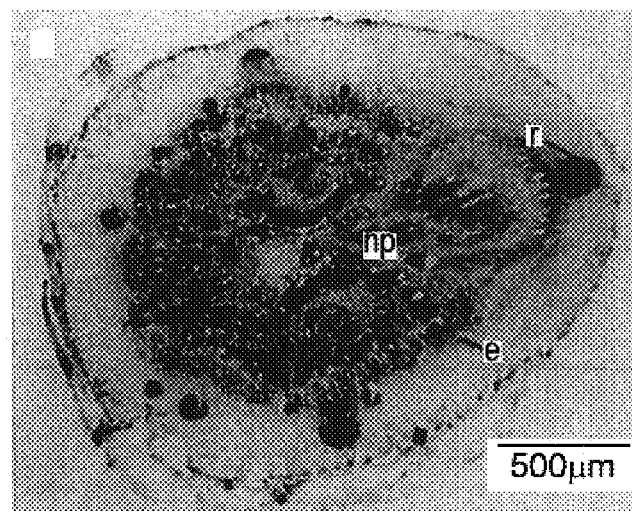

To observe tissue distribution of OsBLE1 and OsBLE2 expression, expression site of the genes was analyzed by in situ hybridization methods. The results showed that OsBLE1 and OsBLE2 were expressed in root primordia and internode parenchyma, which are involved in controlling elongation in rice (FIGS. 4A–4C).

EXAMPLE 6

Figure 5A:
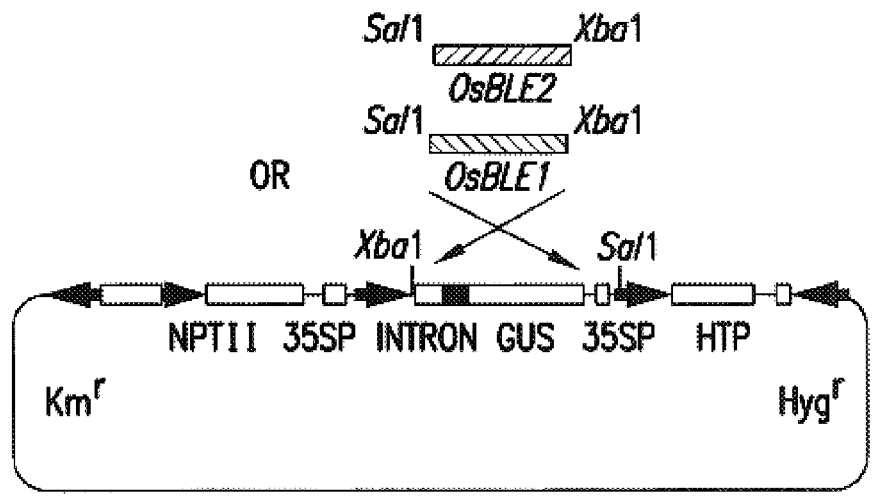
FIG. 5A shows a recombinant binary vector construct.
Figure 5B:
FIGS. 5B and 5C are photographs which show rice plants that were transformed via antisense cDNA of OsBLE1 and OsBLE2 respectively, and that were dwarfed as compared to a control (into which vector control was introduced).
Figure 5C:

Both of cDNAs of OsBLE1 and OsBLE2 were modified to have SalI restriction site at their 5' end and to have XbaI restriction sites at their 3' ends. The modified cDNAs were then digested with XbaI and SalI and inserted into a binary vector pIG121-Hm (Ohta S., Mita S., Hattori T., Nakamura K., Plant Cell Physiol., 31: 805–813, 1990) at XbaI (5' end) and SalI (3' end) sites (in the antisense direction) under the control of cauliflower mosaic virus 35S promoter. The recombinant binary vectors were introduced into *Agrobacterium* EHA101, and the resulting *Agrobacterium* was introduced into *Nipponbare* rice cultivar by ultrahigh-speed transformation method for monocotyledons. As a result, the transformed rice showed suppressed growth of stem and leaf compared to controls containing the vector alone (FIGS. 5A–5C). Therefore, the present inventors have succeeded in dwarfing a transformed plant in which expression of a gene that is induced by addition of a plant hormone, brassinolide, is regulated.

What is claimed is:

1. An isolated polynucleotide selected from the group consisting of:
   (a) a polynucleotide encoding a polypeptide comprising the amino acid sequence of SEQ ID NO:4; and
   (b) a polynucleotide comprising positions 119 to 2401 of the nucleotide sequence of SEQ ID NO:3.

* * * * *

SEQUENCE LISTING

```
<160> NUMBER OF SEQ ID NOS: 4

<210> SEQ ID NO 1
<211> LENGTH: 598
<212> TYPE: DNA
<213> ORGANISM: Oryza sativa
<220> FEATURE:
<223> OTHER INFORMATION: cDNA
<220> FEATURE:
<221> NAME/KEY: CDS
<222> LOCATION: (37)..(282)

<400> SEQUENCE: 1
aattcggcac gagcggcggc gagaggagcg gcggcg atg ggc ggc ggc ggg cac        54
                                        Met Gly Gly Gly Gly His
                                          1               5 ggc ggc ggc acg acg tac aag ggg tac acc atc ccc cac aac aag cgc       102
Gly Gly Gly Thr Thr Tyr Lys Gly Tyr Thr Ile Pro His Asn Lys Arg
           10                  15                  20 tgg cac acc gtc gcc ggc aag ggc ctc tgc gcc gtc atg tgg ttt tgg       150
Trp His Thr Val Ala Gly Lys Gly Leu Cys Ala Val Met Trp Phe Trp
       25                  30                  35 gtt ttc tac agg gct aag cag gac ggt gct gtt ctc ttg ggc atg cgt       198
Val Phe Tyr Arg Ala Lys Gln Asp Gly Ala Val Leu Leu Gly Met Arg
   40                  45                  50 cat cct tgg gat ggt cat gat gat cac tca cat ggt cat ggg cat gag       246
His Pro Trp Asp Gly His Asp Asp His Ser His Gly His Gly His Glu
55                  60                  65                  70 cat gag gga tca tca tca aca tcg tcg tct cac taa atcaactgct            292
His Glu Gly Ser Ser Ser Thr Ser Ser Ser His
               75                  80 tcttggcggc tgagggagac tcgctgcttt ggttgtcgcg atgaaatcct cgaagataat      352
aaagtttcac actattaatt ttattaagat gggttcatgt tgttggcaac tgtttaaggc      412
aaactggtta tgtattttgc ttttgagata gcctccctcg atggaaaacc catgtatgtt      472
gttgcttatt aggctgtgga catccttttg gatgtagagg ctgggttttt aatccattat      532
ctaaaaaaat gttgttgctt cttccgatca aaaaaaaaaa aaaaaaaaaa aaaaaaaaaa      592
aaaaaa                                                                 598

<210> SEQ ID NO 2
<211> LENGTH: 81
<212> TYPE: PRT
```

<213> ORGANISM: Oryza sativa

<400> SEQUENCE: 2

```
Met Gly Gly Gly His Gly Gly Thr Thr Tyr Lys Gly Tyr Thr
 1               5                  10                  15
Ile Pro His Asn Lys Arg Trp His Thr Val Ala Gly Lys Gly Leu Cys
            20                  25                  30
Ala Val Met Trp Phe Trp Val Phe Tyr Arg Ala Lys Gln Asp Gly Ala
        35                  40                  45
Val Leu Leu Gly Met Arg His Pro Trp Asp Gly His Asp Asp His Ser
    50                  55                  60
His Gly His Gly His Glu His Gly Ser Ser Thr Ser Ser Ser
65                  70                  75                  80
His
```

<210> SEQ ID NO 3
<211> LENGTH: 3243
<212> TYPE: DNA
<213> ORGANISM: Oryza sativa
<220> FEATURE:
<223> OTHER INFORMATION: cDNA
<220> FEATURE:
<221> NAME/KEY: CDS
<222> LOCATION: (119)..(2404)

<400> SEQUENCE: 3

| | |
|---|---:|
| aatctctcct ctaggcgtct tttggtatat aggagtatct cggcttgttt gggttgctct | 60 |
| gtacaaatgt gctgaggctt gggttctagg ctggcttacc tatagctagt tagcttac | 118 |

```
atg atg gcc gcc ggt ggc cac gct gcc gcg gag cac cgc ata cag ata       166
Met Met Ala Ala Gly Gly His Ala Ala Ala Glu His Arg Ile Gln Ile
 1               5                  10                  15 cca gct gcc ccg gcg tcg cag tcg gga cca gct gat cat aag gcg gtc       214
Pro Ala Ala Pro Ala Ser Gln Ser Gly Pro Ala Asp His Lys Ala Val
            20                  25                  30 gcc gcg gcg ccg gag aag tgg ctg aat tac ttt ctt cgc ttg ctc gcg       262
Ala Ala Ala Pro Glu Lys Trp Leu Asn Tyr Phe Leu Arg Leu Leu Ala
        35                  40                  45 gtg atc gaa agc gtg ggc aac gcc ttc ggc acg ctg gcc ttc acc tgg       310
Val Ile Glu Ser Val Gly Asn Ala Phe Gly Thr Leu Ala Phe Thr Trp
    50                  55                  60 gcc acc gtc gtc ctg ctg ggt ggc tac cca acc gtt ctc aag cgc gat       358
Ala Thr Val Val Leu Leu Gly Gly Tyr Pro Thr Val Leu Lys Arg Asp
65                  70                  75                  80 ttt ggt att gcg act gcg ata att ttc cta gaa gcc acg agg atg ttc       406
Phe Gly Ile Ala Thr Ala Ile Ile Phe Leu Glu Ala Thr Arg Met Phe
                85                  90                  95 acc cgc aac aat agg ctg gat tat caa ttg ttc ttc cgg acg aga ggt       454
Thr Arg Asn Asn Arg Leu Asp Tyr Gln Leu Phe Phe Arg Thr Arg Gly
            100                 105                 110 gcc ttt aga cca ctg ggc tgg aac ggg ctg atg gta atc gta ttc ttc       502
Ala Phe Arg Pro Leu Gly Trp Asn Gly Leu Met Val Ile Val Phe Phe
        115                 120                 125 tcc gtt tct atg gtg tcc acg gtt gtt tgg gac gca cgc cgg cca cgt       550
Ser Val Ser Met Val Ser Thr Val Val Trp Asp Ala Arg Arg Pro Arg
    130                 135                 140 ata gta ttt cca att atg gta gta ttg ttt gcg gtt ggc cag ttt cta       598
Ile Val Phe Pro Ile Met Val Val Leu Phe Ala Val Gly Gln Phe Leu
145                 150                 155                 160 tgt gct gga gtt cta gga ctg cgc cta cgt atc aac agt cgg tta cgc       646
Cys Ala Gly Val Leu Gly Leu Arg Leu Arg Ile Asn Ser Arg Leu Arg
                165                 170                 175 cgt cag atg tcg ctg tgg agc ccc atg gtt gca atc tta ttg ctg gct       694
Arg Gln Met Ser Leu Trp Ser Pro Met Val Ala Ile Leu Leu Leu Ala
```

-continued

```
                        180                 185                 190
tcc tgt att tgc aga agc tcg cta ctg gcc ata tgg ata gta tat ggt        742
Ser Cys Ile Cys Arg Ser Ser Leu Leu Ala Ile Trp Ile Val Tyr Gly
            195                 200                 205 gtg ctc ctt gtg gtt gtg ctc cta gtg act att agc agg ttg caa ttc        790
Val Leu Leu Val Val Val Leu Val Thr Ile Ser Arg Leu Gln Phe
        210                 215                 220 cca att ata atc aac cga gta cat ggt gct ttg ggc cgc aaa tac gta        838
Pro Ile Ile Ile Asn Arg Val His Gly Ala Leu Gly Arg Lys Tyr Val
225                 230                 235                 240 ttt tgg cgc cca ttt atc cta tac tcg tgc atg ctc gct gca att gtg        886
Phe Trp Arg Pro Phe Ile Leu Tyr Ser Cys Met Leu Ala Ala Ile Val
                245                 250                 255 ttg ccg atg ttc atg att gat aaa tta tat cga tat gcg atc atc gtc        934
Leu Pro Met Phe Met Ile Asp Lys Leu Tyr Arg Tyr Ala Ile Ile Val
            260                 265                 270 ctc gac ata tct gcc ttg gtc att gtg tcc ttc ggt aac cta cag att        982
Leu Asp Ile Ser Ala Leu Val Ile Val Ser Phe Gly Asn Leu Gln Ile
        275                 280                 285 cca gca gca ctc gtg cgt gtt gtg ctc gcg gcg ttg ggc ttt gat caa       1030
Pro Ala Ala Leu Val Arg Val Val Leu Ala Ala Leu Gly Phe Asp Gln
290                 295                 300 gag gac tac gat ggt cac ggt gac acg aca aat ctt ccc caa tct cta       1078
Glu Asp Tyr Asp Gly His Gly Asp Thr Thr Asn Leu Pro Gln Ser Leu
305                 310                 315                 320 act atc ttc tat ggg atg gtg ctt gga caa gga cta ctt tac atc att       1126
Thr Ile Phe Tyr Gly Met Val Leu Gly Gln Gly Leu Leu Tyr Ile Ile
                325                 330                 335 gcc gca gta ttg gag gtc ttc tcg ttc atc cct cgg ata cac ctc gtc       1174
Ala Ala Val Leu Glu Val Phe Ser Phe Ile Pro Arg Ile His Leu Val
            340                 345                 350 cgc cgt ggt gga ttt aca ggt cga tgg gga gca gaa tct gtt gat atg       1222
Arg Arg Gly Gly Phe Thr Gly Arg Trp Gly Ala Glu Ser Val Asp Met
        355                 360                 365 tac tac gca tac gcc tat gac aaa tac atg gaa gga ggt ctg ttt gct       1270
Tyr Tyr Ala Tyr Ala Tyr Asp Lys Tyr Met Glu Gly Gly Leu Phe Ala
370                 375                 380 cca aag agg atc agc ctc agc aac ttt gcc atg gat tct ctg aat tcg       1318
Pro Lys Arg Ile Ser Leu Ser Asn Phe Ala Met Asp Ser Leu Asn Ser
385                 390                 395                 400 gac ctg tcc aag aat cag cta tac ggt gtc cag atg atg cat ata ttt       1366
Asp Leu Ser Lys Asn Gln Leu Tyr Gly Val Gln Met Met His Ile Phe
                405                 410                 415 ctg caa aat ggt ctg acc aag gca cgg ttg ctg gag aaa ctc acc act       1414
Leu Gln Asn Gly Leu Thr Lys Ala Arg Leu Leu Glu Lys Leu Thr Thr
            420                 425                 430 tca acg cag acg atg gcc agg tta atc agc atg ttg gac tgg agt agt       1462
Ser Thr Gln Thr Met Ala Arg Leu Ile Ser Met Leu Asp Trp Ser Ser
        435                 440                 445 aga cat cat cgt gca act atc agg tta tat gcc gcc aag gtc act gcc       1510
Arg His His Arg Ala Thr Ile Arg Leu Tyr Ala Ala Lys Val Thr Ala
450                 455                 460 gag ctt gca aag aac ctc cga gtt gaa act gtc cct ggg aca ctg cag       1558
Glu Leu Ala Lys Asn Leu Arg Val Glu Thr Val Pro Gly Thr Leu Gln
465                 470                 475                 480 ctt gta tct acg ctt ctg gat gct gat gga aag cca aaa aga gga cac       1606
Leu Val Ser Thr Leu Leu Asp Ala Asp Gly Lys Pro Lys Arg Gly His
                485                 490                 495 cca ctc ctg gat gca gat gat gat caa gat cat ttt gtt gat ata gca       1654
```

```
                                                -continued

Pro Leu Asp Ala Asp Asp Gln Asp His Phe Val Asp Ile Ala
        500                 505                 510 gat aga caa gat aaa aga cat gat ata gct ggt aac caa ggg cag aga     1702
Asp Arg Gln Asp Lys Arg His Asp Ile Ala Gly Asn Gln Gly Gln Arg
        515                 520                 525 cga gag ccg att ggg gac acc aat aac ctg ctg gaa aca cca acc cga     1750
Arg Glu Pro Ile Gly Asp Thr Asn Asn Leu Leu Glu Thr Pro Thr Arg
        530                 535                 540 tca aca cac atc aac gac caa aga tac ata cct aga att tgg cag agg     1798
Ser Thr His Ile Asn Asp Gln Arg Tyr Ile Pro Arg Ile Trp Gln Arg
545                 550                 555                 560 ata ctg gag tac tgg tcg att ccc aag gag cag cca ttg aca gac gat     1846
Ile Leu Glu Tyr Trp Ser Ile Pro Lys Glu Gln Pro Leu Thr Asp Asp
                565                 570                 575 gat ctc ctc cct gca cta ggc atg tca atc att tat agc ctt gct ggc     1894
Asp Leu Leu Pro Ala Leu Gly Met Ser Ile Ile Tyr Ser Leu Ala Gly
        580                 585                 590 tgt gat caa aat aat tgt gtg gaa ata gac aga gta act gat ctg atc     1942
Cys Asp Gln Asn Asn Cys Val Glu Ile Asp Arg Val Thr Asp Leu Ile
        595                 600                 605 ccc aat ata att gga ttc aca agc ttc aga agt gca atg gta aat tcc     1990
Pro Asn Ile Ile Gly Phe Thr Ser Phe Arg Ser Ala Met Val Asn Ser
        610                 615                 620 gaa gca caa cag aag gtt ctc tta aag tca tcg ttg aag gta ctg cag     2038
Glu Ala Gln Gln Lys Val Leu Leu Lys Ser Ser Leu Lys Val Leu Gln
625                 630                 635                 640 agg ctc aca agc att gaa ggg gaa att ggc ata aca ctg cgg tac aag     2086
Arg Leu Thr Ser Ile Glu Gly Glu Ile Gly Ile Thr Leu Arg Tyr Lys
                645                 650                 655 ata tca aaa cat ccc ttc tta ctg cga aac ctt gca gag atc ttg cga     2134
Ile Ser Lys His Pro Phe Leu Leu Arg Asn Leu Ala Glu Ile Leu Arg
        660                 665                 670 gac aat agc agc aac aaa caa gaa cta agg aag ctc gtg gta gga atc     2182
Asp Asn Ser Ser Asn Lys Gln Glu Leu Arg Lys Leu Val Val Gly Ile
        675                 680                 685 ctc aga aac ctt gcc att gac aga cac aca agg caa gag atg gga caa     2230
Leu Arg Asn Leu Ala Ile Asp Arg His Thr Arg Gln Glu Met Gly Gln
        690                 695                 700 atg caa atg ctc att acc acg ctg atc aag gca ttc ctc gat ttt aaa     2278
Met Gln Met Leu Ile Thr Thr Leu Ile Lys Ala Phe Leu Asp Phe Lys
705                 710                 715                 720 gga tta ttt agt tca gat gtt gat tgc ttg ctg cca aag gtc gcc ggg     2326
Gly Leu Phe Ser Ser Asp Val Asp Cys Leu Leu Pro Lys Val Ala Gly
                725                 730                 735 caa gca ttg gta atg ctg tca tca gaa aat tcg cat aac tgc ttt gtt     2374
Gln Ala Leu Val Met Leu Ser Ser Glu Asn Ser His Asn Cys Phe Val
        740                 745                 750 atg ttg aag gaa cca gat ttc att cat taa ctaaaaaata tgatcctaat      2424
Met Leu Lys Glu Pro Asp Phe Ile His
        755                 760 ccatggtgat aaatacatat atgtggcagc gagtctattg cgtaatatgt gcctgtatgc   2484
tcaacatgag ctcacagaat cagaccaaaa ggaactatct cacacattgc gagaggtgtt   2544
ggaaagaata atggacactg aaggggcaga actagaaatc ctcattggcc ttagttcaca   2604
gatatgcaaa ctcattcctg aagaattttc ccaagagcta gagcatggac agattaagcg   2664
gagattcatt aagaggctag tggacaccct gaatgcaaac atgaacccaa gttctcattg   2724
ccctgggatc cggagggtgg tacttgagca atccatacac atgatggagt acaattctcg   2784
```

```
ctatgccaat tatttcaatg aataccagat gatggatgca ctgtcgtttg tagaattgac    2844
accctcaagg gctgagaatt acatggtttt cttgggtgac gcaggtttca tggaatgtaa    2904
cacacctctc tctgccctag tggacagggc aaaagaactg atgggtcgtc agtggctgca    2964
aggtatcagc agtgccaact gaaaaaaaat aaaatgtttt tgcatataca gtcagaagac    3024
cttgcatatt gttagtgcag ggcaaacaaa gtgattctgc atttacagtc agaagacaac    3084
gcatgttgct agaagaaaca tatatttacc tttaagatga gcaaagggta ttgtatctgt    3144
acatcatgaa tcttgcactg taatctgtgt gctattgatg atttatccaa ttatcatttg    3204
ttgagtggcc aaaaaaaaaa aaaaaaaaaa aaaaaaaaa                           3243
```

<210> SEQ ID NO 4
<211> LENGTH: 761
<212> TYPE: PRT
<213> ORGANISM: Oryza sativa

<400> SEQUENCE: 4

```
Met Met Ala Ala Gly Gly His Ala Ala Ala Glu His Arg Ile Gln Ile
 1               5                  10                  15

Pro Ala Ala Pro Ala Ser Gln Ser Gly Pro Ala Asp His Lys Ala Val
             20                  25                  30

Ala Ala Ala Pro Glu Lys Trp Leu Asn Tyr Phe Leu Arg Leu Leu Ala
         35                  40                  45

Val Ile Glu Ser Val Gly Asn Ala Phe Gly Thr Leu Ala Phe Thr Trp
     50                  55                  60

Ala Thr Val Val Leu Leu Gly Gly Tyr Pro Thr Val Leu Lys Arg Asp
 65                  70                  75                  80

Phe Gly Ile Ala Thr Ala Ile Ile Phe Leu Glu Ala Thr Arg Met Phe
                 85                  90                  95

Thr Arg Asn Asn Arg Leu Asp Tyr Gln Leu Phe Phe Arg Thr Arg Gly
            100                 105                 110

Ala Phe Arg Pro Leu Gly Trp Asn Gly Leu Met Val Ile Val Phe Phe
        115                 120                 125

Ser Val Ser Met Val Ser Thr Val Val Trp Asp Ala Arg Arg Pro Arg
    130                 135                 140

Ile Val Phe Pro Ile Met Val Val Leu Phe Ala Val Gly Gln Phe Leu
145                 150                 155                 160

Cys Ala Gly Val Leu Gly Leu Arg Leu Arg Ile Asn Ser Arg Leu Arg
                165                 170                 175

Arg Gln Met Ser Leu Trp Ser Pro Met Val Ala Ile Leu Leu Leu Ala
            180                 185                 190

Ser Cys Ile Cys Arg Ser Ser Leu Leu Ala Ile Trp Ile Val Tyr Gly
        195                 200                 205

Val Leu Leu Val Val Leu Leu Val Thr Ile Ser Arg Leu Gln Phe
    210                 215                 220

Pro Ile Ile Ile Asn Arg Val His Gly Ala Leu Gly Arg Lys Tyr Val
225                 230                 235                 240

Phe Trp Arg Pro Phe Ile Leu Tyr Ser Cys Met Leu Ala Ala Ile Val
                245                 250                 255

Leu Pro Met Phe Met Ile Asp Lys Leu Tyr Arg Tyr Ala Ile Ile Val
            260                 265                 270

Leu Asp Ile Ser Ala Leu Val Ile Val Ser Phe Gly Asn Leu Gln Ile
        275                 280                 285

Pro Ala Ala Leu Val Arg Val Val Leu Ala Ala Leu Gly Phe Asp Gln
```

```
            290                 295                 300
Glu Asp Tyr Asp Gly His Gly Asp Thr Thr Asn Leu Pro Gln Ser Leu
305                 310                 315                 320

Thr Ile Phe Tyr Gly Met Val Leu Gly Gln Gly Leu Leu Tyr Ile Ile
                325                 330                 335

Ala Ala Val Leu Glu Val Phe Ser Phe Ile Pro Arg Ile His Leu Val
                340                 345                 350

Arg Arg Gly Gly Phe Thr Gly Arg Trp Gly Ala Glu Ser Val Asp Met
                355                 360                 365

Tyr Tyr Ala Tyr Ala Tyr Asp Lys Tyr Met Glu Gly Gly Leu Phe Ala
370                 375                 380

Pro Lys Arg Ile Ser Leu Ser Asn Phe Ala Met Asp Ser Leu Asn Ser
385                 390                 395                 400

Asp Leu Ser Lys Asn Gln Leu Tyr Gly Val Gln Met Met His Ile Phe
                405                 410                 415

Leu Gln Asn Gly Leu Thr Lys Ala Arg Leu Leu Glu Lys Leu Thr Thr
                420                 425                 430

Ser Thr Gln Thr Met Ala Arg Leu Ile Ser Met Leu Asp Trp Ser Ser
                435                 440                 445

Arg His His Arg Ala Thr Ile Arg Leu Tyr Ala Ala Lys Val Thr Ala
                450                 455                 460

Glu Leu Ala Lys Asn Leu Arg Val Glu Thr Val Pro Gly Thr Leu Gln
465                 470                 475                 480

Leu Val Ser Thr Leu Leu Asp Ala Asp Gly Lys Pro Lys Arg Gly His
                485                 490                 495

Pro Leu Leu Asp Ala Asp Asp Gln Asp His Phe Val Asp Ile Ala
                500                 505                 510

Asp Arg Gln Asp Lys Arg His Asp Ile Ala Gly Asn Gln Gly Gln Arg
                515                 520                 525

Arg Glu Pro Ile Gly Asp Thr Asn Asn Leu Leu Glu Thr Pro Thr Arg
                530                 535                 540

Ser Thr His Ile Asn Asp Gln Arg Tyr Ile Pro Arg Ile Trp Gln Arg
545                 550                 555                 560

Ile Leu Glu Tyr Trp Ser Ile Pro Lys Glu Gln Pro Leu Thr Asp Asp
                565                 570                 575

Asp Leu Leu Pro Ala Leu Gly Met Ser Ile Ile Tyr Ser Leu Ala Gly
                580                 585                 590

Cys Asp Gln Asn Asn Cys Val Glu Ile Asp Arg Val Thr Asp Leu Ile
                595                 600                 605

Pro Asn Ile Ile Gly Phe Thr Ser Phe Arg Ser Ala Met Val Asn Ser
                610                 615                 620

Glu Ala Gln Gln Lys Val Leu Leu Lys Ser Ser Leu Lys Val Leu Gln
625                 630                 635                 640

Arg Leu Thr Ser Ile Glu Gly Glu Ile Gly Ile Thr Leu Arg Tyr Lys
                645                 650                 655

Ile Ser Lys His Pro Phe Leu Leu Arg Asn Leu Ala Glu Ile Leu Arg
                660                 665                 670

Asp Asn Ser Ser Asn Lys Gln Glu Leu Arg Lys Leu Val Val Gly Ile
                675                 680                 685

Leu Arg Asn Leu Ala Ile Asp Arg His Thr Arg Gln Glu Met Gly Gln
                690                 695                 700

Met Gln Met Leu Ile Thr Thr Leu Ile Lys Ala Phe Leu Asp Phe Lys
705                 710                 715                 720
```

-continued

```
Gly Leu Phe Ser Ser Asp Val Asp Cys Leu Leu Pro Lys Val Ala Gly
                725                 730                 735

Gln Ala Leu Val Met Leu Ser Ser Glu Asn Ser His Asn Cys Phe Val
            740                 745                 750

Met Leu Lys Glu Pro Asp Phe Ile His
        755                 760
```